United States Patent [19]

Smith

[11] Patent Number: 5,736,112
[45] Date of Patent: Apr. 7, 1998

[54] AQUEOUS OXIDATION OF ORGANIC MOLYBDENUM COMPOUNDS

[75] Inventor: William Allen Smith, Round Rock, Tex.

[73] Assignee: Huntsman Specialty Chemicals Corporation, Austin, Tex.

[21] Appl. No.: 436,538

[22] Filed: May 8, 1995

[51] Int. Cl.[6] .................................................. B01D 11/00
[52] U.S. Cl. .............................................. 423/54; 423/606
[58] Field of Search .................. 423/606, 54; 549/529; 556/57

[56] References Cited

U.S. PATENT DOCUMENTS

| | | | |
|---|---|---|---|
| 3,453,068 | 7/1969 | Tave | 23/30 |
| 3,573,226 | 3/1971 | Sorgenti | 252/431 |
| 3,819,663 | 6/1974 | Levine et al. | 260/348.51 |
| 3,887,361 | 6/1975 | Lemke | 75/108 |
| 3,931,044 | 1/1976 | Maurin | 252/414 |
| 4,328,191 | 5/1982 | Su et al. | 423/54 |
| 4,401,631 | 8/1983 | Canavent et al. | 423/54 |
| 4,455,283 | 6/1984 | Sweed | 423/53 |
| 4,485,074 | 11/1984 | Poenisch | 423/55 |
| 4,661,463 | 4/1987 | Mocella | 502/24 |
| 5,093,509 | 3/1992 | Meyer et al. | 556/57 |
| 5,101,052 | 3/1992 | Mayer et al. | 549/529 |
| 5,128,492 | 7/1992 | Smith et al. | 549/529 |
| 5,232,559 | 8/1993 | Smith et al. | 204/59 M |

*Primary Examiner*—Deborah Jones
*Assistant Examiner*—Amy M. Harding
*Attorney, Agent, or Firm*—Russell R. Stolle; Ron D. Brown; Carl G. Ries

[57] ABSTRACT

Molybdenum oxides are recovered from an organic solvent solution of organic molybdenum compounds by adding the organic solvent solution to water and reacting the organic molybdenum compounds therein with oxygen under pressure to convert the organic components of the organic molybdenum compounds to carbon dioxide and water and to convert the molybdenum components to molybdenum oxides, and to form an aqueous solution of molybdenum oxides from which the molybdenum oxides can be recovered.

7 Claims, 1 Drawing Sheet

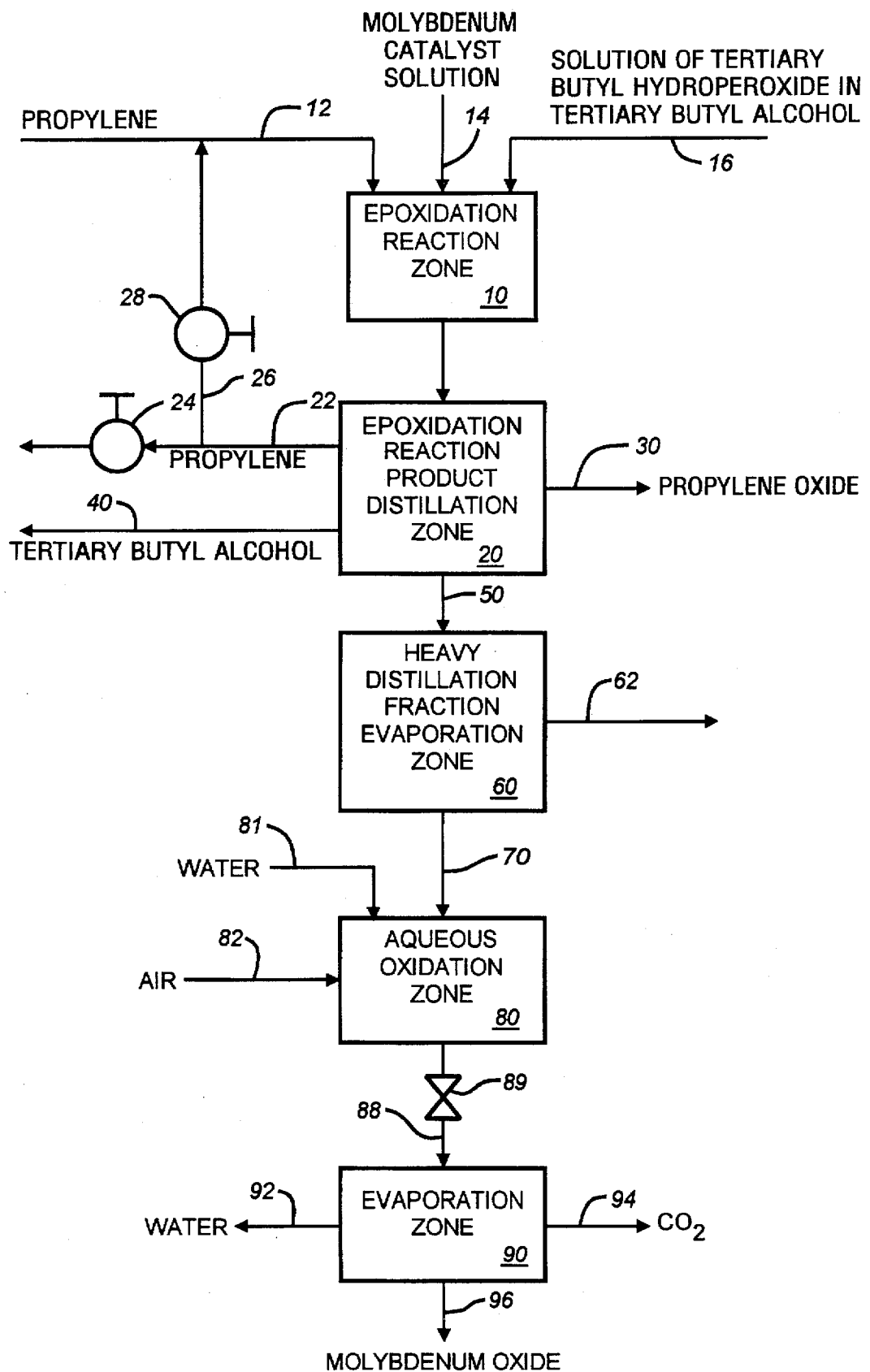

AQUEOUS OXIDATION OF ORGANIC MOLYBDENUM COMPOUNDS

BACKGROUND OF THE INVENTION

1. Field of the Invention

This invention relates to a process for the aqueous oxidation of organic molybdenum compounds. More particularly, this invention relates to an aqueous oxidation process for the conversion of organic molybdenum compounds to molybdenum oxides and to the recovery of the thus-formed molybdenum oxides. Still more particularly, this invention relates to an aqueous oxidation process for the conversion of residual organic molybdenum compounds contained in an organic solvent in order to form molybdenum oxides and to the recovery of the thus-formed molybdenum oxides. With greater particularity, this invention relates to a process for the conversion by aqueous oxidation of residual organic molybdenum catalyst compounds contained in an organic residue fraction formed as part of a propylene epoxidation process in order to form molybdenum oxides and to the recovery of the thus-formed molybdenum oxides.

Molybdenum compounds are somewhat toxic to livestock and, therefore, solutions containing molybdenum must be handled with care. Also, the presence of molybdenum in liquid by-products presents a disposal problem because of the limited toxicity of molybdenum to livestock.

The epoxidation reaction mixture that is formed when propylene is reacted with tertiary butyl hydroperoxide in solution in tertiary butyl alcohol in the presence of a soluble molybdenum epoxidation catalyst will normally comprise unreacted propylene, propylene oxide, tertiary butyl alcohol, unreacted tertiary butyl hydroperoxide, the soluble molybdenum catalyst and impurities, including $C_1$ to $C_4$ lower aliphatic carboxylic acids. The reaction mixture is usually separated by distillation into a plurality of fractions including a recycle propylene fraction, a propylene oxide product fraction, a tertiary butyl alcohol product fraction and a heavy liquid distillation fraction containing tertiary butyl alcohol, unreacted tertiary butyl hydroperoxide and impurities, including substantially all of the dissolved molybdenum catalyst and a portion of the lower aliphatic carboxylic acid impurities.

In accordance with the present invention, an organic solvent solution of organic molybdenum compounds, such as organic molybdates, is added to water and oxidized with oxygen under pressure to convert the organic components of the organic molybdenum compounds to carbon dioxide and water and to convert the molybdenum components to molybdenum oxides for subsequent recovery.

In accordance with a preferred embodiment of the present invention, a heavy liquid distillation fraction formed during a propylene epoxidation process and comprising tertiary butyl alcohol, tertiary butyl hydroperoxide, other oxygen-containing organic compounds and dissolved organic molybdenum catalyst residue compounds are added to water and the resultant mixture is oxidized with oxygen under pressure to convert the organic compounds to carbon dioxide and water and to convert the molybdenum to recoverable molybdenum oxides.

Prior Art

It is known to react propylene with tertiary butyl hydroperoxide in the presence of a soluble molybdenum catalyst to provide a reaction product comprising propylene oxide and tertiary butyl alcohol. See, for example, Kollar U.S. Pat. No. 3,350,422, Kollar U.S. Pat. No. 3,351,635, and Russell U.S. Pat. No. 3,418,340.

It is also known to prepare soluble molybdenum catalysts to catalyze the reaction as disclosed, for example, in Bonetti et al. U.S. Pat. No. 3,480,563, Shum et al. U.S. Pat. No. 4,607,113, Marquis et al. U.S. Pat. No. 4,626,596, Marquis et al. U.S. Pat. No. 4,650,886, Marquis et al. U.S. Pat. No. 4,703,027, etc.

Sorgenti U.S. Pat. No. 3,573,226 discloses a method wherein a molybdenum-containing catalyst solution is prepared by incorporating metallic molybdenum into the distillate bottoms fraction of an epoxidation reaction product followed by heating of the resultant mixture in order to form a soluble molybdenum-containing reaction product which can be used to catalyze the epoxidation reaction.

Maurin U.S. Pat. No. 3,931,044 is directed to a method for recovering molybdenum catalyst values from a epoxidation reaction product for recycle. Maurin discloses one of three techniques. In accordance with the first embodiment, the residue fraction is calcined to provide molybdenum trioxide which is then used to prepare a soluble molybdenum compound by reaction with aqueous ammonia. In a second embodiment, the molybdenum-containing fraction is treated with aqueous ammonia without calcining to form an ammonium molybdate which is treated with a polyalcohol to give a molybdic ester. In a third embodiment, the molybdenum-containing fraction is treated with gaseous ammonia in order to form an ammonium molybdate precipitate which can be recovered by filtration.

Levine U.S. Pat. No. 3,819,663 is directed to a method for treating a heavy distillation fraction in order to recover the molybdenum in the concentrated bottoms fraction for recycle to the epoxidation reaction zone as makeup catalyst.

Levine conducts his wiped-film evaporation process under conditions including a temperature of about 550°–650° F. (about 273° to about 330° C.) at atmospheric pressure to obtain his desired residual fraction for recycle as catalyst makeup and a distillate fraction comprising about 85% or more of the heavy distillation fraction. Levine states that the distillate fraction that is thus obtained can be used as a furnace fuel or can be worked up for recovery of the individual components contained therein.

Su et al. in U.S. Pat. No. 4,328,191, disclose a method for recovering molybdenum from an epoxidation catalyst residue wherein the epoxidation residue is brought into contact with an oxidizing agent such as hydrogen peroxide, nitric acid or sodium hypochlorite. The molybdenum is thereafter recovered by liquid-liquid or liquid-solid extraction.

In Canavent et al. U.S. Pat. No. 4,401,631, a molybdenum residue is solubilized with an aqueous alkali metal hydroxide and the resultant solution, after filtration, is brought into contact with a strong cationic exchange resin to convert the molybdenum compounds to molybdic acid.

Sweed U.S. Pat. No. 4,455,283 discloses a process for recovering molybdenum values from a crude reaction product by vacuum evaporation.

Synthetic high surface area amorphous magnesium silicates are used in a process disclosed in Meyer et al. U.S. Pat. No. 5,093,509 to remove molybdenum from an epoxidation residue fraction.

In Meyer et al. U.S. Pat. No. 5,101,052, an epoxidation residue fraction is saturated with ammonia to precipitate molybdenum therefrom for recovery.

In Smith et al. U.S. Pat. No. 5,128,492, an epoxidation residue fraction is saturated with hydrogen to precipitate molybdenum therefrom.

In Smith et al. U.S. Pat. No. 5,232,559, an epoxidation residue fraction is saturated with ammonia to precipitate molybdenum which is recovered therefrom by filtration, the filtrate still contains dissolved molybdenum and is added to an electrolytic cell. A direct electric current is passed through the filtrate to collect a significant portion of the remaining molybdenum at the cathode of the cell.

SUMMARY OF THE INVENTION

In accordance with the present invention, recoverable molybdenum oxides are prepared by adding an organic solvent solution of organic molybdenum compounds to water and by oxidizing the molybdenum compounds with molecular oxygen under pressure to convert the organic components of the organic molybdenum compounds to carbon dioxide and water and to convert the molybdenum components to recoverable molybdenum oxides. The molybdenum oxides may be recovered from the aqueous solution in any suitable fashion. For example, water may be boiled from the aqueous solution to form precipitated molybdenum oxides which may be recovered for disposal.

In accordance with a preferred embodiment of the present invention, a heavy liquid distillation fraction formed during a propylene epoxidation process and comprising tertiary butyl alcohol, tertiary butyl hydroperoxide, other oxygen-containing organic compounds and dissolved organic molybdenum catalyst residue compounds is added to water and the resultant mixture is oxidized with oxygen under pressure to convert the organic compounds to carbon dioxide and water and to convert the molybdenum to recoverable molybdenum oxides.

Background Information

When propylene is reacted with tertiary butyl hydroperoxide in solution in tertiary butyl alcohol in an epoxidation reaction zone in the presence of a soluble molybdenum catalyst to form propylene oxide and additional tertiary butyl alcohol, an epoxidation reaction mixture is formed which will contain not only unreacted feed components and the desired propylene oxide and tertiary butyl alcohol, but also impurities including the dissolved molybdenum catalyst, oxygen-containing impurities such as ditertiary butyl peroxide, lower aliphatic $C_1$ to $C_4$ carboxylic acids such as formic acid, acetic acid, isobutyric acid, etc., alcohols such as methanol, isopropyl alcohol, tertiary butyl alcohol, etc., esters such as methyl formate, methyl acetate, methyl isobutyrate, etc., ketones such as acetone, etc., aldehydes such as isobutyraldehyde, etc., and hydrocarbon impurities resulting from undesired side reactions of the propylene, such as hydrocarbons containing 6 or more carbon atoms.

Although most of the impurities are originally present in the epoxidation reaction mixture in trace quantities, as the epoxidation reaction mixture is resolved by distillation into a propylene recycle fraction, a propylene oxide product fraction and a tertiary butyl alcohol product fraction, all of which are distillate fractions, the higher boiling impurities are progressively concentrated in a heavier distillation fraction, such as a distillation fraction having the composition generally set forth in Table I.

TABLE I

| COMPOSITION OF HEAVY DISTILLATION FRACTIONS | |
|---|---|
| Component | Concentration, Wt. % |
| Impurities lighter than TBA | 0.1–2 |
| Tertiary butyl alcohol | 70–90 |
| Impurities heavier than TBA but lighter than TBHP | 1–4 |
| Tertiary butyl hydroperoxide | 2–20 |
| Impurities heavier than TBHP | 3–12 |
| Molybdenum concentration | 500–5,000 ppm |

In the work-up of the epoxidation reaction product formed by the epoxidation of propylene with tertiary butyl hydroperoxide in the presence of a soluble molybdenum catalyst to form propylene oxide and tertiary butyl alcohol, a heavy organic stream is produced that contains spent organic molybdenum catalyst. Methods for the direct concentration of the molybdenum in the heavy organic stream are limited in that the molybdenum can be concentrated only to about 8 wt. %. Attempts to further concentrate the molybdenum (e.g., by evaporation) will normally result in the formation of intractable tars that are difficult to handle and that tend to foul the evaporation equipment.

Incineration of organic molybdenum concentrates also presents problems in that the combustion products tend to corrode the equipment and in that the incinerator must be equipped with a flue gas bag house to capture any molybdenum trioxide or other volatile molybdenum compounds that may be present in the flue gas.

DETAILED DESCRIPTION

In accordance with the present invention, recoverable, molybdenum compounds are prepared by adding an organic solvent solution of organic molybdenum compounds to water and by oxidizing the molybdenum compounds with molecular oxygen under pressure to convert the organic components of the organic molybdenum compounds to carbon dioxide and water and to convert the molybdenum components to recoverable molybdenum oxides.

The reaction conditions may suitably include a temperature of about 200° to about 450° C., a pressure of about 1000 to about 6000 psig. and a reaction time within the range of about 0.5 to 5 hours correlated so as to substantially completely convert the organic components of the molybdenum compounds to carbon dioxide and water and to convert the molybdenum components to recoverable molybdenum oxides. More preferably, the reaction conditions will include a temperature of about 350° to about 450° C., a pressure of about 3000 to about 6000 psig. and a reaction time within the range of about 2 to 5 hours.

The molybdenum oxides may be recovered from the aqueous solution in any suitable fashion. For example, water may be boiled from the aqueous solution to form precipitated molybdenum oxides which may be recovered by decantation, centrifugation, filtration, etc. for disposal or for reformulation into active epoxidation catalyst.

In accordance with a preferred embodiment of the present invention, a heavy liquid distillation fraction formed during a propylene epoxidation process and comprising tertiary butyl alcohol, tertiary butyl hydroperoxide, other oxygen-containing organic compounds and dissolved organic molybdenum catalyst residue compounds is added to water and the resultant mixture is oxidized with oxygen under pressure, as described above, to convert the organic compounds to carbon dioxide and water and to convert the molybdenum to recoverable molybdenum oxides.

BRIEF DESCRIPTION OF THE DRAWING

In the drawing, the FIGURE is a schematic drawing of a preferred reaction and oxidation sequence that may be used in the practice of the present invention.

An epoxidation reaction zone 10 is provided and propylene is charged thereto by a line 12 together with a soluble molybdenum catalyst charged by a line 14. A solution of tertiary butyl hydroperoxide in tertiary butyl alcohol is charged by a line 16.

The epoxidation reaction is an epoxidation reaction of the type disclosed by Kollar U.S. Pat. No. 3,351,635, as further elaborated upon, for example, in British patent specification No. 1,298,253 wherein propylene is reacted with tertiary butyl hydroperoxide under reaction conditions including a reaction temperature within the range of about 180° to about 300° F., a pressure of about 300 to about 1000 psig. and, more preferably, a temperature of about 220° F. to about 280° F. and a pressure of about 500 to about 800 psig. As another example, the epoxidation of propylene with tertiary butyl hydroperoxide in solution in tertiary butyl alcohol in the presence of a soluble molybdenum catalyst is disclosed in Marquis et al. U.S. Pat. No. 4,891,437. See also, Marquis et al. U.S. Pat. No. 4,845,251.

The soluble molybdenum catalyst charged to the epoxidation reaction zone by the line 14 may be an epoxidation catalyst of the type known in the art such as those disclosed by the Kollar patent or the British patent or by Marquis et al. U.S. Pat. No. 4,626,596, U.S. Pat. No. 4,650,886, U.S. Pat. No. 4,654,427, U.S. Pat. No. 4,703,027, or U.S. Pat. No. 4,758,681. The Marquis et al. patents are directed to molybdenum/alkanol complexes such as solutions of molybdenum compounds in ethylene glycol which contain a high concentration of molybdenum and are particularly useful as catalysts in the epoxidation reaction. Marquis et al. teach, for example, the epoxidation of propylene with tertiary butyl hydroperoxide with their catalyst under epoxidation conditions including a temperature of 50° to 180° C. and a use of propylene to tertiary butyl hydroperoxide ratios within the range of about 0.9:1 to about 3.0:1.

Thus, the organic molybdenum compounds that are used as catalysts include organic compounds such as molybdenum naphthenates, stearates, octoates, carbonyls and the like, such as molybdenum naphthenate, molybdenum hexacarbonyl, etc. The reaction products of molybdenum oxides, such as molybdenum trioxide with $C_4$ to $C_{22}$ alkanols such as butanol, octanol, dodecanol, 2-hexanol, etc., can be used, as well as the reaction products of molybdenum oxides with alkylene glycol monoalkyl ethers such as ethylene glycol monomethyl ether, diethylene glycol monomethyl ether, propylene glycol monomethyl ether, butylene glycol monomethyl ether, ethylene glycol monobutyl ether, etc. Other organic molybdenum compounds that can be used include complexes of ammonium molybdates such as ammonium heptamolybdate, ammonium dimolybdates, etc., with alkylene glycols such as ethylene glycol, propylene glycol, 1,4-butane diol, 2,3-butane diol, 1,2-cyclohexane diol, etc.

Suitably, the tertiary butyl hydroperoxide that is charged to the epoxidation reaction zone 10 by way of line 16 is about a 40 to about 75 wt. % solution of tertiary butyl hydroperoxide in tertiary butyl alcohol. The catalyst is charged to the epoxidation reaction zone 10 by the charge line 14 in an amount such as to provide from about 50 to about 1000 ppm of molybdenum, based on the total of the reactants charged and, more preferably, from about 200 to 600 ppm. The reaction is preferably conducted at superatmospheric pressure such as a pressure of about 300 to 1000 psig.

When the reaction in conducted on a continuous basis, as illustrated in the drawing, the feed materials are charged to the epoxidation reaction zone 10 through the lines 12, 14 and 16 at rates sufficient to maintain the desired concentration of reactants and an equivalent volume of epoxidation reaction mixture is withdrawn from the epoxidation reaction zone 10 by way of a discharge line 18. The reaction product discharged by the line 18 will normally comprise unreacted propylene, a minor amount of unreacted tertiary butyl hydroperoxide, propylene oxide, tertiary butyl alcohol, including tertiary butyl alcohol formed by the reaction of the tertiary butyl hydroperoxide with propylene, the molybdenum catalyst and impurities such as propane, propionaldehyde, acetone, methanol, isopropanol, water, acetaldehyde, methyl formate, acetic acid, formic acid, isobutyric acid, hydrocarbons containing 6 or more carbon atoms and high boiling residue components.

The reaction product 18 is charged to an epoxidation reaction product distillation zone 20 where it is separated by distillation into desired fractions in accordance with methods known to those skilled in the art. For example, the distillation sequence disclosed in British Patent No. 1,298,253 may be used.

One of the distillate products that is recovered in the zone 20 is a propylene fraction which is discharged by a line 22 controlled by a valve 24 and provided with a branch line 26 controlled by a valve 28 in order to permit the recycle of unreacted propylene to the epoxidation reaction zone 10 through the propylene charge line 12.

Another distillate fraction that is obtained is a propylene oxide product fraction 30 which is discharged by the line 30.

The propylene oxide fraction may be purified in a propylene oxide purification zone (not shown) by known techniques such as, for example, those disclosed in Burnes et al. U.S. Pat. No. 3,715,284, Schmidt et al. U.S. Pat. No. 3,909,366, Schmidt U.S. Pat. No. 3,881,996, Jubin U.S. Pat. No. 3,607,669, Schmidt U.S. Pat. No. 3,843,488 or Schmidt U.S. Pat. No. 4,140,588.

Another product that is recovered from the epoxidation reaction product distillation zone 20 is a tertiary butyl alcohol distillate product 40 which may be further purified, if desired, to remove oxygenated impurities therefrom by catalytic treatment as disclosed, for example, in Sanderson et al. U.S. Pat. No. 4,704,482, Sanderson et al. U.S. Pat. No. 4,705,903 or Sanderson et al. U.S. Pat. No. 4,742,149.

A heavy distillation fraction 50, usually a bottoms fraction, is also discharged from the epoxidation reaction product distillation zone 20. As described by Levine U.S. Pat. No. 4,455,283, the heavy distillation fraction will contain substantially all of the molybdenum catalyst initially charged to the epoxidation reaction zone 10 by way of the line 14. The heavy distillation fraction 50 will contain other products such as tertiary butyl hydroperoxide, tertiary butyl alcohol and impurities including oxygenates lighter than tertiary butyl alcohol such as acetaldehyde, acetone, isopropyl alcohol, etc. Oxygenates heavier than tertiary butyl alcohol, but lighter than tertiary butyl hydroperoxide, and residue components heavier than tertiary butyl hydroperoxide such as propylene glycol, tertiary butyl ethers, etc. As indicated, the heavy distillation fraction 50 will also contain carboxylic acids such as formic acid, acetic acid and isobutyric acid.

Although the molybdenum catalyst is present in the epoxidation reaction zone 10 in an amount in the range of about 50 to 1,000 ppm, it is progressively concentrated in the epoxidation reaction product distillation zone 20 and is normally present in the heavy distillation fraction 50 in an amount in the range of about 0.4 to about 0.8 wt. % (about 4,000 to 8,000 ppm).

In accordance with the present invention, the heavy distillation fraction 50 is charged to a heavy distillation evaporation zone 60 which may comprise, for example, a wiped-film evaporator, a falling film evaporator, a forced circulation evaporator, etc., which is operated at a subatmospheric pressure within the range of about 2 to about 200 mm Hg. and a temperature of about 50° to about 160° C. with a residence time such that from about 60 to about 95 wt. % of the heavy distillation fraction charged by the line 50 is taken overhead as condensate by a discharge line 62. The remaining 40 to 5 wt. % of the charge 50 will be discharged by way of a line 70 and will contain substantially all of the molybdenum initially charged to the epoxidation reaction zone 10.

When the heavy distillation fraction 50 is subjected to evaporation in the described manner and under the conditions described above, decomposition of tertiary butyl hydroperoxide to tertiary butyl alcohol and/or decomposition of tertiary butyl alcohol to isobutylene is substantially inhibited so that decomposition of the bottom fraction charged to the evaporator by the line 50 is minimal.

The liquid residue from the evaporation conducted in the evaporation zone 60 will comprise an organic solvent solution of soluble organic molybdenum compounds containing about 0.1 to about 5 wt. % of dissolved molybdenum. As measured by the TOC test, the "Total Organic Carbon" in the molybdenum solution is about 50 to about 80 wt. %. In accordance with the present invention, the organic solvent solution of soluble organic molybdenum compounds is removed from the evaporator 60 by a line 70 leading to an aqueous oxidation reaction zone 80 together with water charged by the line 81; the water being charged in an amount sufficient to provide about 5 to 200 parts by weight of water, per part of the organic solvent solution of soluble organic molybdenum compounds. A feed stream comprising oxygen, such as a stream of air, is charged by a line 82 and oxidation reaction conditions are established in the oxidation reaction zone 80, including a temperature of about 200° to about 450° C., a pressure of about 1000 to 6000 psig and a residence time of about 0.5 to 5 hours. More preferably, the reaction temperature will be maintained at about 350° to about 450° C. and the pressure will be maintained at about 3000 to 5000 psig. Under these reaction conditions, the organic components of the organic solvent solution of soluble organic molybdenum compounds will react with the oxygen and form a reaction product comprising molybdenum oxides, carbon dioxide and water.

The reaction product formed in the aqueous oxidation zone is discharged by a line 88 containing a pressure release valve 89 leading to an evaporation zone 90. Oxygen is charged to the aqueous oxidation zone 80 by line 82 at the rate of about 2 to 3 lbs. of oxygen per pound of catalyst residue. Within the evaporation zone 90, an off-gas comprising carbon dioxide will evolve and will be discharged from the zone 90 by a line 94 and water is evaporated for removal through a line 92 to provide an aqueous or solid concentrate of molybdenum oxides. Water may be removed in the evaporation zone by spray evaporation, for example, or by using a wiped-film evaporator, a falling film evaporator, a forced circulation evaporator, etc., of the type employed in the heavy distillation fraction evaporation zone 60.

The molybdenum oxides in the line 96 are recovered for shipment, for example, to a molybdenum reclaimer or may be reformulated into fresh epoxidation catalyst using the process discussed by Marquis et al. U.S. Pat. No. 4,654,427.

EXAMPLE

Four experimental runs were made to demonstrate the oxidation of a molybdenum containing organic stream.

In the first run, 200 g of deionized water and 4 g of spent molybdenum catalyst residue containing 3.4 wt. % Mo was added to a 500 ml autoclave which, after sealing, was pressured with oxygen to 500 psi while still at room temperature. The reactor was then heated to the desired temperature for two hours and cooled. The reaction product was analyzed for total organic carbon (TOC). In the last three runs, the feed mixture was used 200 g of deionized water, 2 gm of the same catalyst residue, and 2 g of methanol. The methanol was added to improve the solubility of the catalyst residue in the water and to make the relatively viscous residue more flowable. Otherwise, the procedure remained the same.

The results from each oxidation run are listed in the following table:

TABLE II

| High Pressure Run Number | Initial TOC of Aqueous Sol. (ppm) (est.) | Temp. (°C.) | Time (hr) | Pressure (psig) | Final TOC (ppm) |
| --- | --- | --- | --- | --- | --- |
| 32955 | 13,000 | 200 | 2 | 1025 | 6,225 |
| 32957 | 13,000 | 250 | 2 | 1425 | 4,200 |
| 32964 | 13,000 | 300 | 2 | 2250 | 1,575 |
| 33045 | 13,000 | 350 | 2 | 3535 | 497 |

As can be seen from the data, it is possible to substantially oxidize the organics in a spent molybdenum containing epoxidation catalyst stream. With the organics in the spent catalyst stream substantially oxidized to carbon dioxide and water, the soluble and insoluble molybdenum oxides which remain may be recovered by simple evaporation. The concentrated molybdenum oxides may be sold to a reclaimer.

Having this described my invention, what is claimed is:

1. A method for the recovery of molybdenum oxides from an organic solvent solution of organic molybdenum compounds containing about 0.1 to about 5.0 wt. % of molybdenum, which comprises the steps of:

adding said organic solvent solution of organic molybdenum compounds to about 5 to about 200 parts of water per part of organic solvent solution and reacting the organic molybdenum compounds therein with oxygen at a temperature of about 200° to about 450° C. and a pressure of about 1000 to about 6000 psig. for a reaction time within the range of about 0.5 to 5 hours sufficient to substantially convert the organic components of the organic molybdenum compounds to carbon dioxide and water and to convert the molybdenum components to molybdenum oxides to thereby form an aqueous reaction product containing molybdenum oxides, and removing water from said aqueous reaction product to form concentrated molybdenum oxides.

2. A method as in claim 1 wherein the temperature is in the range of about 350° to about 450° C. and the pressure is within the range of about 3000 to about 5000 psig.

3. A method as in claim 1 wherein the water and $CO_2$ are removed by evaporation.

4. In a process for the preparation of propylene oxide and tertiary butyl alcohol wherein propylene and tertiary butyl hydroperoxide are reacted in an epoxidation reaction zone in solution in tertiary butyl alcohol in the presence of a soluble molybdenum catalyst to provide an epoxidation reaction product comprising propylene oxide, unreacted propylene, unreacted tertiary butyl hydroperoxide, tertiary butyl alcohol, dissolved molybdenum catalyst and impurities and wherein the epoxidation reaction product is resolved into product fractions in a distillation zone including a distillate propylene oxide fraction, a distillate propylene fraction, a distillate tertiary butyl alcohol fraction, and a heavy liquid distillation fraction comprising tertiary butyl hydroperoxide, tertiary butyl alcohol and impurities including dissolved molybdenum catalyst, and wherein said heavy liquid distillation fraction is fractionated under sub-atmospheric conditions to provide a liquid residue fraction containing organic molybdenum compounds and containing about 0.1 to 5 wt. % of molybdenum, the improvement which comprises:

adding said liquid residue fraction to about 5 to about 200 parts of water per part of liquid residue fraction and reacting the organic molybdenum compounds therein with oxygen at a temperature of about 200° to about 450° C. and a pressure of about 1000 to about 6000 psig. for a reaction time within the range of about 0.5 to 5 hours sufficient to substantially convert the organic components of the organic molybdenum compounds to carbon dioxide and water and to convert the molybdenum components to molybdenum oxides to thereby form an aqueous reaction product containing molybdenum oxides, and removing water from said aqueous reaction product to form concentrated molybdenum oxides.

5. A method as in claim 4 wherein the liquid residue fraction contains about 50–80 wt. % of Total Organic Carbon (TOC).

6. A method as in claim 5 wherein the temperature is in the range of about 350° to about 450° C. and the pressure is within the range of about 3000 to about 5000 psig.

7. A method as in claim 6 wherein the water is removed by evaporation.

* * * * *